United States Patent
Villeger et al.

(10) Patent No.: US 10,456,491 B2
(45) Date of Patent: *Oct. 29, 2019

(54) METHOD OF STERILIZING AN OBJECT WITH ATOMIC NITROGEN FROM A NITROGEN PLASMA

(71) Applicant: SOCIETE POUR LA CONCEPTION DES APPLICATIONS DES TECHNIQUES ELECTRONIQUES, Merignac (FR)

(72) Inventors: Sandrine Villeger, Montjoire (FR); Marie-Agnès Benoit, Merignac (FR); Pascal Regere, Blanquefort (FR)

(73) Assignee: Societe Pour La Conception Des Applications Des Techniques Electroniques, Merignac (FR)

( * ) Notice: Subject to any disclaimer, the term of this patent is extended or adjusted under 35 U.S.C. 154(b) by 6 days.

This patent is subject to a terminal disclaimer.

(21) Appl. No.: 15/832,148

(22) Filed: Dec. 5, 2017

(65) Prior Publication Data

US 2019/0142983 A1 May 16, 2019

(30) Foreign Application Priority Data

Nov. 14, 2017 (FR) .................... 17 60684

(51) Int. Cl.
*A61L 2/14* (2006.01)
*A61L 2/26* (2006.01)
(Continued)

(52) U.S. Cl.
CPC .............. *A61L 2/14* (2013.01); *A61L 2/24* (2013.01); *A61L 2/26* (2013.01); *H05H 1/00* (2013.01);
(Continued)

(58) Field of Classification Search
CPC ...... A61L 2/14; A61L 2/26; A61L 2/24; A61L 2202/122; A61L 2202/24
See application file for complete search history.

(56) References Cited

U.S. PATENT DOCUMENTS 4,756,882 A 7/1988 Jacobs et al.
5,186,893 A 2/1993 Moulton et al.
(Continued)

FOREIGN PATENT DOCUMENTS

KR 100920917 B1 * 10/2009
KR 100920917 B1 10/2009

OTHER PUBLICATIONS

KR-100920917 Translation (Year: 2009).*
(Continued)

*Primary Examiner* — Sean E Conley
*Assistant Examiner* — Brendan A Hensel
(74) *Attorney, Agent, or Firm* — Workman Nydegger

(57) ABSTRACT

A method of sterilizing an object with atomic nitrogen from a nitrogen plasma includes the steps of placing the object in a sterilization chamber and a sterilization half-cycle for sterilizing the object present in the chamber. The sterilization half-cycle comprises an alternation between stages of injecting atomic nitrogen into the chamber and of intermediate stages, each intermediate stage including at least one suction stage during which the chamber is evacuated.

10 Claims, 2 Drawing Sheets

(51) Int. Cl.
   *H05H 1/00*   (2006.01)
   *A61L 2/24*   (2006.01)
(52) U.S. Cl.
   CPC ..... *A61L 2202/122* (2013.01); *A61L 2202/24* (2013.01)

(56) References Cited

U.S. PATENT DOCUMENTS

| | | | | |
|---|---|---|---|---|
| 5,645,796 | A * | 7/1997 | Caputo | A61L 2/14 422/22 |
| 6,365,102 | B1 * | 4/2002 | Wu | A61L 2/14 422/23 |
| 2011/0014093 | A1 * | 1/2011 | Ono | A61L 2/18 422/292 |
| 2011/0027125 | A1 * | 2/2011 | Golkowski | A61L 2/208 422/29 |

OTHER PUBLICATIONS

Sirajuddin, Plasma Sterilization (Year: 2007).*
Bockel et al., "Optical Diagnostics of Active Species in N2 Microwave Flowing Post-Discharges," Surface and Coatings Technology, vol. 74-75, 1995, pp. 474-478.
French Search Report from FR Application No. FR 1760684, dated Jul. 20, 2018.

* cited by examiner

METHOD OF STERILIZING AN OBJECT WITH ATOMIC NITROGEN FROM A NITROGEN PLASMA

FIELD OF THE INVENTION

The present invention relates to a method of sterilizing an object by injecting atomic nitrogen from a nitrogen plasma.

BACKGROUND OF THE INVENTION

It is known to sterilize objects by means of an autoclave in which the object that is to be sterilized is raised to a determined high temperature, of about 120° C., with this lasting for determined periods of time and with cycles that are set out by legislation.

Applying a high temperature can raise difficulties and can lead to certain objects being damaged, e.g. when those objects include portions made of polymer material.

Methods that enable sterilization to be performed at lower temperatures have consequently been developed in order to reduce the damage to objects while they are being treated.

In this context, methods of sterilization have been developed by treating the object with a stream of atomic nitrogen from a nitrogen plasma.

Nevertheless, it remains desirable to improve the effectiveness of sterilization by known methods, in particular by reducing the treatment time.

In addition, certain known methods may present a phenomenon of saturation insofar as there may always remain some quantity of microorganisms that are not destroyed by the sterilization treatment, even if the treatment is prolonged. It would be desirable to have a method with improved sterilization effectiveness, without such a saturation phenomenon.

OBJECT AND SUMMARY OF THE INVENTION

In a first aspect, the invention provides a method of sterilizing an object with atomic nitrogen from a nitrogen plasma, the method comprising at least:

placing the object in a sterilization chamber; and a sterilization half-cycle for sterilizing the object present in the chamber, the sterilization half-cycle comprising an alternation between stages of injecting atomic nitrogen into the chamber and of intermediate stages, each intermediate stage including at least one suction stage during which the chamber is evacuated.

The term "atomic nitrogen" should be understood as the nitrogen that is obtained after dissociating dinitrogen $N_2$ (i.e. the element N). By definition, a "sterilization half-cycle" enables the number of microorganisms present to be subjected to a 6 log reduction relative to the start of the half-cycle.

The inventors have found that performing a succession of injections of atomic nitrogen separated by stages of suction imparts improved sterilization effectiveness, while making it possible during sterilization to use a temperature that is limited, less than 60° C.

In an implementation, each intermediate stage further comprises a stage of injecting molecular nitrogen into the chamber.

The term "molecular nitrogen" should be understood as nitrogen in the dinitrogen state (i.e. the molecule $N_2$).

Performing such an intermediate stage serves to further improve the effectiveness of the sterilization.

In particular, each intermediate stage may comprise:

a first suction stage during which the chamber is evacuated; p a stage of injecting molecular nitrogen into the chamber that is performed after the first suction stage; and a second suction stage performed after the stage of injecting molecular nitrogen, and during which the chamber is evacuated.

Performing such an intermediate stage serves to still further improve the effectiveness of the sterilization.

In particular, each stage of injecting molecular nitrogen may have a duration that is shorter than at least one of the durations of the stages of injecting atomic nitrogen. In particular, each stage of injecting molecular nitrogen may have a duration that is shorter than each of the durations of the stages of injecting atomic nitrogen.

In an implementation, each half-cycle comprises at least:

a first set of stages of injecting atomic nitrogen during which a first atomic nitrogen concentration is imposed in the chamber; and a second set of stages of injecting atomic nitrogen that is performed after the first set, and during which a second atomic nitrogen concentration is imposed in the chamber, the second concentration being higher than the first concentration.

The atomic nitrogen concentrations imposed in the chamber may be measured using a spectrophotometer. By way of example, it is possible to use the method described in the publication by Bockel et al.: "Optical diagnostics of active species in $N_2$ microwaves flowing post-discharge" (S. Bockel, A. M. Diamy, and A. Ricard: Surface and coatings technology, 74-75 (1995), 474-478) in order to measure such concentrations of atomic nitrogen.

The increase in the concentration of atomic nitrogen that is imposed in the chamber during the stages of injecting of atomic nitrogen serves to still further improve the effectiveness of the sterilization.

In an implementation, the pressure in the chamber reached during each of the stages of injecting atomic nitrogen is greater than or equal to 10 millibars (mbar).

In an implementation, the pressure in the chamber reached during each of the suction stages is less than or equal to 1 mbar.

In an implementation, each stage of injecting atomic nitrogen has a duration lying in the range 5 minutes (min) to 30 min, and the half-cycle includes at least three stages of injecting atomic nitrogen.

In particular, each stage of injecting atomic nitrogen has a duration lying in the range 5 min to 15 min, and the half-cycle includes at least four stages of injecting atomic nitrogen, e.g. at least six stages of injecting atomic nitrogen.

In an implementation, each stage of injecting molecular nitrogen has a duration lying in the range 1 min to 5 min.

In an implementation, the object is a medical instrument.

BRIEF DESCRIPTION OF THE DRAWINGS

Other characteristics and advantages of the invention appear from the following description given in non-limiting manner with reference to the accompanying drawings, in which.

DETAILED DESCRIPTION OF EMBODIMENTS

Figure 1:
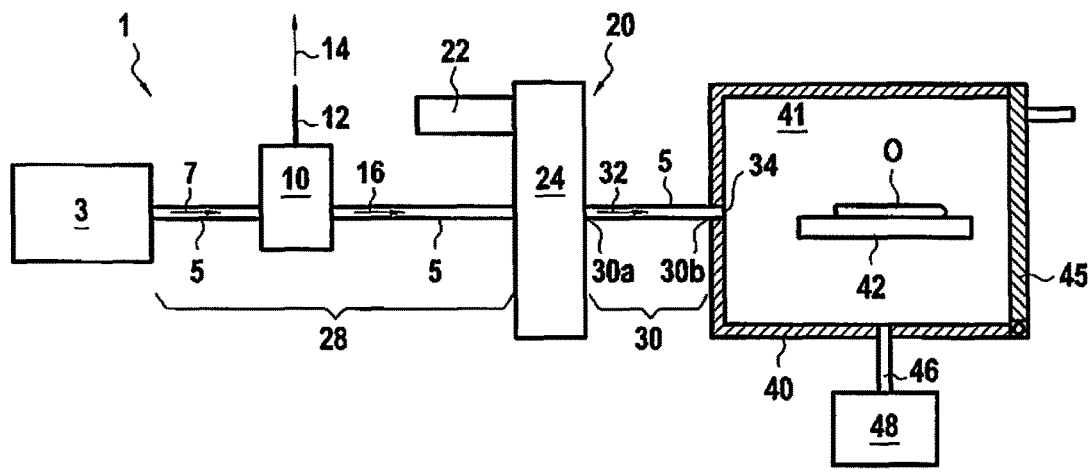
FIG. 1 is a diagram showing an example of a sterilization device suitable for performing a sterilization method of the invention.

FIG. 1 is a diagram of a sterilization device 1 configured to sterilize an object O by treatment with a post-discharge stream of a nitrogen plasma. Such a post-discharge stream comprises a mixture of neutral species, namely atomic nitrogen N and dinitrogen $N_2$.

The device 1 comprises a duct 5 having a first segment 28 putting a compressor 3 into communication with a plasma generator 20. The first segment 28 is provided with a nitrogen filter element 10 situated between the compressor 3 and the plasma generator 20.

A stream 7 of compressed air coming from the compressor 3 flows through the first segment 28 to the filter element 10. The filter element 10 is constituted by an element that is itself known and that is configured to separate dinitrogen from oxygen in the stream 7 of compressed air. After passing through the filter element 10, a stream of dinitrogen 16 flows through the first segment 28 to the plasma generator 20. The oxygen 14 that has been separated from the nitrogen is discharged via an exhaust duct 12.

The first segment 28 enables the stream 16 of dinitrogen to be admitted into the plasma generator 20. The volume content of dinitrogen in the dinitrogen stream 16 admitted into the plasma generator 20 may be greater than or equal to 95%, or indeed greater than or equal to 99%. The dinitrogen stream 16 admitted into the plasma generator 20 may include residual oxygen at a volume content that is less than or equal to 1%. In a variant, the dinitrogen stream 16 admitted into the plasma generator 20 may have no oxygen. In known manner, the plasma generator 20 serves to generate a nitrogen plasma from the nitrogen stream 16. The plasma generator 20 comprises an evacuated enclosure 24 subjected to the action of an electromagnetic field generator that is constituted in this example by a microwave generator 22. The electromagnetic field generated in the enclosure 24 is of sufficiently high intensity to cause the nitrogen to ionize.

The duct has a second segment 30 that puts the plasma generator 20 into communication with a sterilization chamber 40 in which the object O for sterilizing is positioned. The post-discharge stream 32 from the nitrogen plasma flows to the sterilization chamber 40 via the second segment 30.

The sterilization chamber 40 defines a treatment zone 41 including at least one support 42 on which the object O is positioned during the sterilization treatment. The figure shows a treatment zone 41 having a single support 42 and a single object O, however it would naturally not go beyond the ambit of the invention for the treatment zone to have a plurality of supports, each carrying one or more objects. The sterilization chamber 40 is provided with a door 45 to enable the object O to be inserted into the treatment zone 41, and to enable it to be removed after sterilization.

The object O may be a medical instrument such as an endoscope, a chisel, or a scalpel. The invention is also advantageous for sterilizing objects other than medical instruments, such as electronic cards.

The second segment 30 presents a proximal end 30a situated beside the plasma generator 20 and in communication therewith. The second segment 30 also presents a distal end 30b defining an injection orifice 34 for injecting the post-discharge stream 32 into the sterilization chamber 40. The plasma generated by the plasma generator 20 penetrates into the second segment 30 via the proximal end 30a. While the plasma that has been formed is flowing through the second segment 30, ionic and metastable species are destroyed by colliding with one another or with the walls of the duct 5. As a result, an electrically neutral post-discharge stream comprising both atomic nitrogen N and dinitrogen $N_2$ is injected into the chamber 40 via the injection orifice 34. The post-discharge stream 32 flows through the second segment 30 and is injected into the sterilization chamber 40 through the injection orifice 34. The treatment zone 41 is in communication with a vacuum pump 48. This pump draws the post-discharge stream 32 into the treatment zone 41 via a second duct 46 and discharges the gas to the outside.

The example device 1 shown in FIG. 1 has a single injection orifice 34. Naturally, it would not go beyond the ambit of the invention for the post-discharge stream to be injected through a plurality of injection orifices 34.

The example device 1 shown in FIG. 1 serves to inject a post-discharge stream from a nitrogen plasma into the sterilization chamber 40. Under such circumstances, the atomic nitrogen injected during stages of injecting atomic nitrogen forms part of a post-discharge stream from a nitrogen plasma. Nevertheless, it would not go beyond the ambit of the invention for the injected atomic nitrogen to be part of a nitrogen plasma.

An example method of the invention is described with reference to FIG. 2.

Prior to the beginning of the half-cycle DC1, the method may include a preliminary step EP of reducing pressure, during which the pressure inside the chamber 40 is reduced from atmospheric pressure Pa to a vacuum pressure Pv. This pressure reduction may be performed in non-monotonic manner and may include brief increases of pressure in the chamber 40, as shown. The vacuum pressure Pv reached at the end of this preliminary step EP may be less than or equal to 1 mbar.

The half-cycle DC1 comprises a plurality of successive stages of injecting atomic nitrogen IA1 and IA2. The stages of injecting atomic nitrogen IA1 and IA2 alternate with intermediate stages I1 and I2 during a given half-cycle DC1. The intermediate stages I1 and I2 each comprise at least one suction stage A1 or A2 during which the chamber 40 is evacuated. Each intermediate stage I1 or I2 is performed between two consecutive stages IA1 or IA2 of injecting atomic nitrogen. The half-cycle DC1 thus comprises in succession a first stage IA1 or IA2 of injecting atomic nitrogen, then an intermediate stage I1 or I2, then a second stage IA1 or IA2 of injecting atomic nitrogen, and then once more an intermediate stage I1 or I2, and so on.

Figure 2:
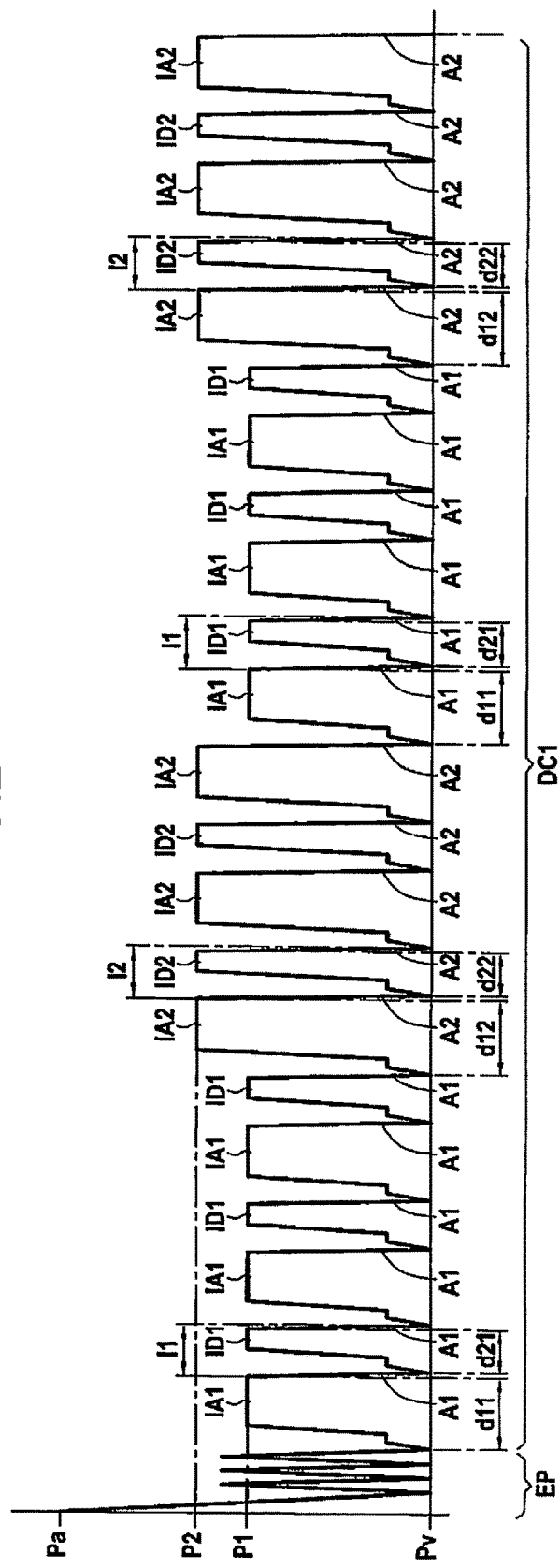
FIG. 2 shows how pressure in the sterilization chamber varies during an example sterilization method of the invention.

In the example shown in FIG. 2, each intermediate stage I1 or I2 comprises in succession a first suction stage A1 or A2, a stage ID1 or ID2 of injecting molecular nitrogen, and a second suction stage A1 or A2. In the example of FIG. 2, two consecutive stages IA1 or IA2 of injecting atomic nitrogen are separated by the following succession of steps:

a first suction stage A1 or A2 during which the chamber 40 is evacuated;

a stage ID1 or ID2 of injecting molecular nitrogen, performed after the first suction stage A1 or A2; and a second suction stage A1 or A2, performed after the stage ID1 or ID2 of injecting molecular nitrogen, and during which the chamber 40 is evacuated.

There follows a detailed description of the sequencing of a first stage IA1 or IA2 of injecting atomic nitrogen, followed by an intermediate stage I1 or I2, and a second stage of injecting atomic nitrogen consecutive with the first stage. For reasons of concision, this sequencing is described only in the context of two consecutive stages of injecting atomic nitrogen, it being understood that this sequencing is repeated in similar manner throughout the half-cycle DC1.

In the example shown, the pressure in the chamber 40 increases from the vacuum pressure Pv to a level value P1 or P2 during each injection stage IA1 or IA2. The pressure in the chamber 40 is then stabilized at the level value P1 or P2 during each injection stage IA1 or IA2. This level value may be greater than or equal to 10 mbar. The duration $d_{11}$ or $d_{12}$ of each injection stage IA1 or IA2 may be greater than or equal to 5 min, for example, and in particular it may lie in the range 5 min to 15 min, for example.

Thereafter, the injection of atomic nitrogen into the chamber 40 is interrupted.

Thereafter, a first suction stage A1 or A2 is performed during which the chamber 40 is evacuated. In this example, the pressure in the chamber 40 decreases progressively from the level value P1 or P2 that was reached during the stage IA1 or IA2, down to the vacuum pressure Pv. The vacuum pressure Pv reached at the end of the first suction stage A1 may be less than or equal to 1 mbar.

The half-cycle DC1 is then continued by injecting dinitrogen into the chamber 40 (stage ID1 or ID2 of injecting molecular nitrogen). During the stage ID1 or ID2, the nitrogen is injected in the form of dinitrogen and no longer in atomic form. During the stages of injecting molecular nitrogen, the dinitrogen stream 16 is injected directly into the chamber 40, with the plasma generator 20 being switched off during these stages, unlike stages of injecting atomic nitrogen in which the plasma generator 20 is activated.

In this example, the pressure in the chamber 40 increases from the vacuum pressure Pv to a level value P1 or P2 during the stage ID1 or ID2 of injecting molecular nitrogen. The pressure in the chamber 40 is then stabilized at this level value P1 or P2 during the stage ID1 or ID2 of injecting molecular nitrogen. This level value may be greater than or equal to 10 mbar. In this example, a level value reached during the stages ID1 of injecting molecular nitrogen is shown as being identical to the value reached during the stages IA1 of injecting atomic nitrogen (value P1), nevertheless it would not go beyond the ambit of the invention if this were not so. In this example, a level value reached during the stages ID2 of injecting molecular nitrogen is shown as being identical to the value reached during the stages IA2 of injecting atomic nitrogen (value P2), but it would nevertheless not go beyond the ambit of the invention if this were not so. By way of example, the duration $d_{21}$ or $d_{22}$ of the stage ID1 or ID2 of injecting molecular nitrogen may be less than or equal to 5 min, and may lie in the range 1 min to 5 min, for example.

Thereafter, the injection of molecular nitrogen into the chamber 40 is interrupted.

Thereafter, a second suction stage A2 is performed during which the chamber 40 is evacuated. In this example, the pressure in the chamber 40 decreases progressively from the level value P1 or P2 that was reached during the stage ID1 or ID2 of injecting molecular nitrogen down to the vacuum pressure Pv. The vacuum pressure Pv reached at the end of this second suction stage A2 may be less than or equal to 1 mbar.

After the second suction stage A2, the second stage IA1 or IA2 of injecting atomic nitrogen is performed with the pressure being stabilized at P1 or P2 in the same manner as described above.

The half-cycle DC1 is then continued by performing a new intermediate stage and then a third injection IA1 or IA2 of atomic nitrogen, and so on, in similar manner to that described above.

In this example, the pressure in the chamber 40 is stabilized on a level value P1 or P2 during each stage IA1 or IA2 of injecting atomic nitrogen. In the example shown, the level value P2 is also higher than the level value P1.

In this example, the half-cycle DC1 comprises at least a first set of successive stages IA1 of injecting atomic nitrogen. During the injection stages IA1 of the first set, a first concentration of atomic nitrogen in the chamber 40 is imposed. The half-cycle DC1 also includes a second set of successive stages IA2 of injecting atomic nitrogen that are performed after the first set of injection stages IA1. During the stages IA2 of injecting atomic nitrogen in the second set, a second concentration of atomic nitrogen in the chamber is imposed, the second concentration being greater than the first concentration.

This increase in the concentration of atomic nitrogen during the injection stages IA2 is represented in this example by an increase in the pressure that is reached in the chamber (going from the pressure P1 to the pressure P2). The concentration of atomic nitrogen can thus be increased during the injection stages IA2 by imposing an injection flow rate of atomic nitrogen during these stages IA1 that is greater than the flow rate of atomic nitrogen that is imposed during the injection stages IA1. This increase in the injection flow rate can be obtained by increasing the flow rate of the air stream 7, and thus of the dinitrogen stream 16. This increase in the injection flow rate results in an increase in pressure in the chamber 40. In a variant, or in combination with such an increase in flow rate, it is possible to decrease the intensity of the suction via the vacuum pump 48 in order to increase the concentration of atomic nitrogen and increase the pressure in the chamber.

Nevertheless, it would not go beyond the ambit of the invention if the pressure reached during the stages IA2 of injecting atomic nitrogen in the second set were not greater than the pressure reached during the injection stages IA1 of the first set. Particularly, it is possible to modulate the imposed concentration of atomic nitrogen by modifying the power of the microwave generator 22 used for forming the plasma upstream from the chamber 40. It is thus possible to increase the concentration of atomic nitrogen during the injection stages IA2 of the second set by increasing this power but without simultaneously increasing the pressure in the chamber.

In addition, in the example shown, the half-cycle DC1 comprises in succession performing the first set of injection stages IA1, then the second set of injection stages IA2, then once more the first set of injection stages IA1, then once more the second set of injection stages IA2. In a variant that is not shown, it would be possible during the half-cycle to perform only one first set of stages IA1 and only one second set of stages IA2. In yet another variant, the atomic nitrogen concentration in the chamber 40 that is imposed during the stages of injecting atomic nitrogen is not caused to vary.

By way of illustration, and regardless of the implementation under consideration, the atomic nitrogen concentration imposed during each of the stages IA1 or IA2 of injecting atomic nitrogen may be greater than or equal to $10^{13}$ atoms per cubic centimeter (atom/cm$^3$), and may for example lie in the range $10^{13}$ atom/cm$^3$ to $10^{16}$ atom/cm$^3$.

Furthermore, there is shown an example half-cycle DC1 in which each intermediate stage I1 or I2 comprises a stage of injecting molecular nitrogen ID1 or ID2 between the first and second suction stages A1 or A2. In the example shown, the durations of the stages ID1 or ID2 are shorter than each of the durations of the stages IA1 and IA2. It would not go beyond the ambit of the invention for each intermediate stage to comprise a stage of injecting molecular nitrogen and at least one suction stage performed before or after each stage of injecting molecular nitrogen. It would nevertheless not go beyond the ambit of the invention for the intermediate stage not to have a stage of injecting molecular nitrogen. It would thus be possible to have an intermediate stage comprising a single suction stage between two consecutive stages of injecting atomic nitrogen.

As mentioned above, a sterilization half-cycle DC1 serves to provide a 6 log reduction in the number of microorganisms. In the context of the invention, it is possible to perform a single sterilization half-cycle. In a variant, the method may include a second sterilization half-cycle identical to the first half-cycle and performed after it. A stage of raising the inside of the chamber 40 to atmospheric pressure Pa may be performed between the first and second half-cycles. When two successive half-cycles are performed, a 12 log reduction obtained of the number of microorganisms present is obtained compared with the beginning of the first half-cycle.

Figure 3:
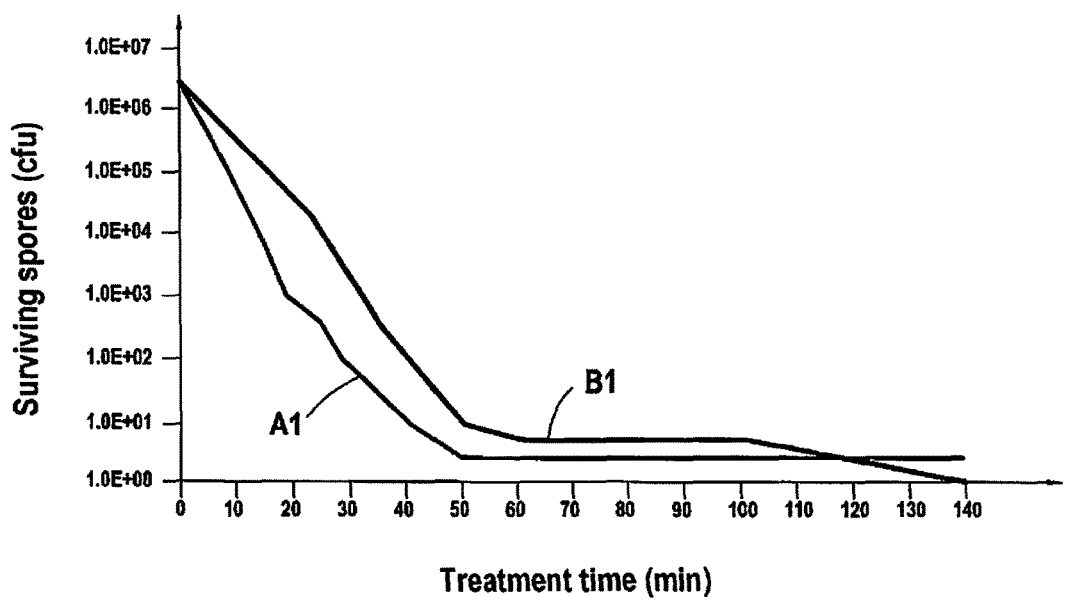
FIG. 3 shows the results obtained in terms of sterilization in the context of the method example shown in FIG. 2.

FIG. 3 shows an experimental result showing the improvement in the effectiveness of sterilization associated with performing a method as shown in FIG. 2.

In this graph, the ordinate axis represents colony forming units (cfu) and the abscissa axis represents treatment time. The strain used was a strain of *geobacillus stearothermophillus*. Curve A1 (not the invention) relates to performing sterilization by injecting atomic nitrogen continuously while maintaining a pressure in the chamber equal to 10 mbar during injection. Curve B1 (the invention) relates to performing a half-cycle DC1 as shown in FIG. 2. In the test performed for the curve B1:
   the pressure P1 was 10 mbar;
   the pressure P2 was 12 mbar;
   the pressure Pv was 0.3 mbar;
   the durations $d_{11}$ and $d_{12}$ were 10 min;
   the durations $d_{21}$ and $d_{22}$ were 2 min;
   the durations of each of the suction stages A1 and A2 were equal to 30 seconds (s); and
   the temperature imposed during sterilization was less than 60° C.

For curve A1, it can be seen that there is a saturation phenomenon starting from about 50 min. This saturation means that there always remains some quantity of microorganisms that are not destroyed by the sterilization treatment, even if it is extended. When implementing the invention, curve B1 shows that saturation is no longer encountered and that a sterile state (6 log reduction) can be obtained.

The expression "lying in the range . . . to . . . " should be understood as including the bounds.

The invention claimed is:

1. A method of sterilizing an object with atomic nitrogen from a nitrogen plasma, the method comprising:
   placing the object in a sterilization chamber; and
   sterilizing the object present in the sterilization chamber in a sterilization half-cycle comprising an alternation between stages of injecting atomic nitrogen into the sterilization chamber and of intermediate stages, each intermediate stage including at least one suction stage during which the sterilization chamber is evacuated,
   wherein each intermediate stage further comprises a stage of injecting molecular nitrogen into the sterilization chamber,
   wherein the injected atomic nitrogen comes from or is part of a nitrogen plasma generated by a plasma generator from a nitrogen stream, and
   wherein said nitrogen stream is injected into the sterilization chamber with the plasma generator being switched off during the stage of injecting molecular nitrogen.

2. The method according to claim 1, wherein each intermediate stage comprises:
   a first suction stage during which the sterilization chamber is evacuated;
   a stage of injecting molecular nitrogen into the sterilization chamber that is performed after the first suction stage; and
   a second suction stage performed after the stage of injecting molecular nitrogen, and during which the sterilization chamber is evacuated.

3. The method according to claim 1, wherein each stage of injecting molecular nitrogen has a duration that is shorter than at least one of the durations of the stages of injecting atomic nitrogen.

4. The method according to claim 1, wherein each half-cycle comprises:
   a first set of stages of injecting atomic nitrogen during which a first atomic nitrogen concentration is imposed in the sterilization chamber; and
   a second set of stages of injecting atomic nitrogen that is performed after the first set, and during which a second atomic nitrogen concentration is imposed in the sterilization chamber, the second concentration being higher than the first concentration.

5. The method according to claim 1, wherein the pressure in the sterilization chamber reached during each of the stages of injecting atomic nitrogen is greater than or equal to 10 mbar.

6. The method according to claim 1, wherein the pressure in the sterilization chamber reached during each of the suction stages is less than or equal to 1 mbar.

7. The method according to claim 1, wherein each stage of injecting atomic nitrogen has a duration in the range 5 min to 30 min, and wherein the half-cycle includes at least three stages of injecting atomic nitrogen.

8. The method according to claim 7, wherein each stage of injecting atomic nitrogen has a duration lying in the range 5 min to 15 min, and wherein the half-cycle includes at least four stages of injecting atomic nitrogen.

9. The method according to claim 1, wherein each stage of injecting molecular nitrogen has a duration lying in the range 1 min to 5 min.

10. The method according to claim 1, wherein the object is a medical instrument.

* * * * *